Figure 2:
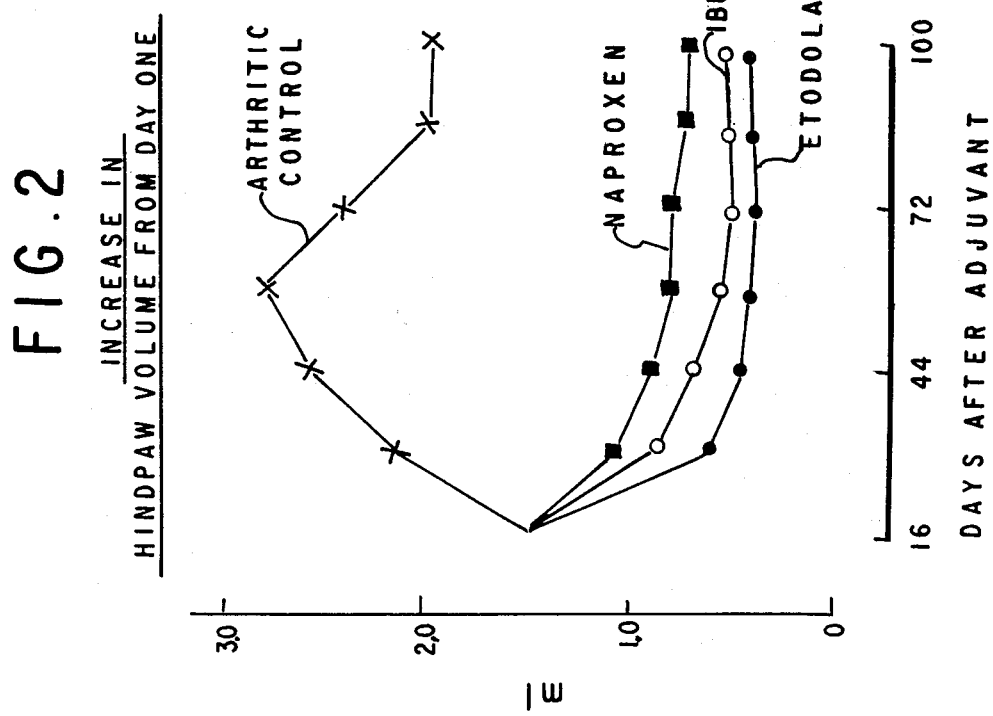

United States Patent [19]

Martel

[11] Patent Number: 4,533,551
[45] Date of Patent: Aug. 6, 1985

[54] METHOD OF TREATING ARTHRITIS WITH ETODOLAC

[75] Inventor: René Martel, Candiac, Canada

[73] Assignee: American Home Products Corporation, New York, N.Y.

[21] Appl. No.: 581,448

[22] Filed: Feb. 17, 1984

[51] Int. Cl.$^3$ ............................................. A61K 31/40
[52] U.S. Cl. .................................... 514/411; 514/825
[58] Field of Search ................................ 424/262, 274

[56] References Cited

PUBLICATIONS

Chem. Abst. 96-154981q (1982), 97-84945a (1982) & 99-151827v (1983).

Primary Examiner—Stanley J. Friedman
Attorney, Agent, or Firm—Walter Patton

[57] ABSTRACT

The effect of prolonged treatment with etodolac on the articular pathology associated with adjuvant arthritis in the rat has been compared to the effects produced by similar treatment with naproxen and ibuprofen. Drug effects were assessed by radiologic and histopathologic examinations. The effects on hindpaw edema, hindleg function, and body weight gain were also evaluated. Treatment was initiated on day 16 after adjuvant injection and continued for 28, 56 or 84 days. The degree of relapse which occurred during 28 days of non-treatment after dosage was stopped after 28 or 56 days of treatment was also assessed. Etodolac prevented the progression of the disease. Further, it appeared to diminish the severity of the articular lesions already present on day 16 before drug treatment began. All the parameters measured were improved and there was good agreement between the radiologic and histopathologic assessments of articular damage. The onset of drug activity was more rapid with etodolac than with the other drugs. By comparison naproxen and ibuprofen decreased edema, increased hindleg function and body weight gain and inhibited the progression of joint damage, but neither drug consistently decreased the magnitude of the articular damage present on day 16. With all three drugs there was less resurgence of disease symptoms when treatment was stopped after 56 days rather than 28 days of drug administration.

3 Claims, 6 Drawing Figures

METHOD OF TREATING ARTHRITIS WITH ETODOLAC

BACKGROUND OF THE INVENTION

Following treatment of adjuvant arthritic rats with the novel antiinflammatory drug etodolac (1,8-diethyl-1,3,4,9-tetrahydropyrano[3,4-b]indole-1-acetic acid, Ultradol ®) there was less bone and articular damage than before the start of treatment. Thus after 28 days dosage etodolac appeared to produce some reversal of the articular pathology already present 16 days after the initiation of the disease. In the same experiment naproxen stopped the further progression of the joint pathology but did not reduce it, while aspirin merely prevented the damage from progressing to maximum intensity. For the present study the period of treatment has been extended (from day 16 up to day 100 after adjuvant) to ascertain whether a longer treatment period could reduce further the joint pathology. In addition the possibility of recurrence of the disease was explored by stopping treatment after different time intervals. The effects produced by etodolac have been compared to the results achieved by naproxen and ibuprofen under the same experimental conditions. The effects of the different treatment on joint damage were assessed by radiologic and histopathologic methods at the end of each experimental period. The evolution of the disease were also monitored by measuring hindleg volume, hindleg function and body weight periodically.

DETAILS OF THE INVENTION

Experimental protocol

Figure 1:
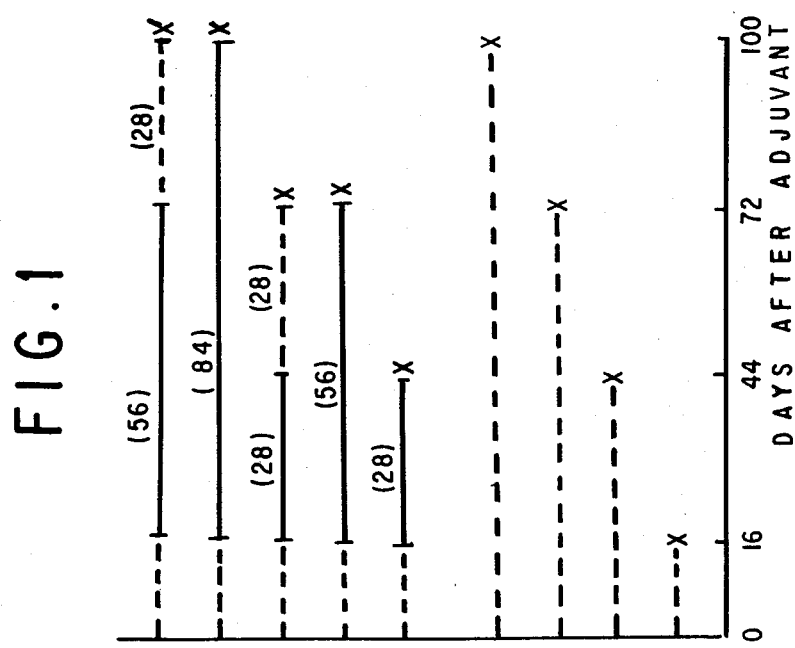

The experimental protocol is summarized in FIG. 1. The disease-induced bone and articular damage in non-treated arthritic control rats was assessed on day 16, 44, 72 and 100 after injection of the adjuvant. For the drug treated groups drug administration was initiated on day 16 when the disease was established. 1,8-Diethyl-1,3,4,9-tetrahydropyrano[3,4-b]indole-1-acetic acid (etodolac) and 6-methoxy-α-methyl-2-naphthaleneacetic acid (naproxen) were administered at 8 mg/kg/day p.o. and α-methyl-4-(2-methylpropyl)benzeneacetic acid (ibuprofen) at 50 mg/kg from day 16–44 (i.e., 28 days treatment), from day 16–72 (56 days treatment) and from 16–100 (84 days treatment) before joint pathology was measured. In addition, drug treatment was stopped in some groups after 28 or 56 days and these groups were left untreated for a further 28 days before pathological examination to ascertain whether there was any re-emergence of the disease process after the cessation of drug treatment. Normal control rats were assessed for joint and bone pathology on day 16 and day 100.

Induction of adjuvant arthritis

Male inbred Wistar Lewis rats (180–220 g, initial weight) obtained from Charles River Breeding Laboratories, Boston, Mass., were injected intradermally in the distal third of the tail with 0.1 ml of Freund's Complete Adjuvant (FCA) composed of a fine suspension of killed and dried *Mycobacterium butyricum* (Difco) in liquid paraffin at a concentration of 5 mg/ml. The day of FCA injection was designated as day 0 of the experiments.

Selection of rats for the experiments

On day 16 after administration of FCA, the volume of both hindpaws was measured by mercury displacement according to the method of Hall, J. M. and Hallett, C.: A simple precise method for measuring rodent paw volume, J. Pharm. Pharmacol. 27:623 (1975).

Only the rats with well established arthritis (mean increase in volume of both hindpaws between 1 and 2.5 ml as compared with the values on day 0) and with similar edema volumes in the left and right hindpaws were selected for the experiment. Animals were distributed into experimental groups of 8 rats so that all groups had comparable mea hindpaw edema volume. On day 16 the mean increase in hindpaw volume (edema) for the 19 groups of 8 rats used in these experiments varied from $1.44 \pm 0.11$ to $1.59 \pm 0.12$ ml and their body weights form $185 \pm 3.3$ to $206 \pm 3.2$ g. A treatment schedule was assigned at random to each group according to the experimental protocol.

Disease progression

Starting on day 16 and at weekly intervals thereafter the progression or the regression was monitored by measuring the three following parameters: hindpaw edema volume, body weight and hindleg function. The increase in hindpaw volume from day 0 was measured in ml as described earlier. Hindleg function was evaluated by the ability of the animals to use their hindlimbs to climb a screen inclined at an angle of 45°. All animals treated with FCA had lost this ability by day 16 so that recovery of hindlimb function represented some degree of remission of the disease. Assessments were made by an observer unaware of the drug treatment. A score of 0 was given if the rats could not climb the screen. Rats were given a score of 1 if they could use their hindlegs to climb the screen and 2 if they climbed the screen without any visible signs of disability. Body weight was measured in grams.

Terminal assessment of pathological changes

On the last day of each experiment the animals were killed using $CO_2$ inhalation. Both hindlimbs were severed above the ankle (tibiotalar) joint and fixed in 10% buffered formalin for radiologic and histopathologic assessment of disease-induced changes. All assessments were made without knowledge of treatment.

(a) Radiologic analysis

Radiographs of hindpaws were obtained with a Picker Standard diagnostic unit. The radiographic changes in both hindlegs were evaluated using a magnifying glass. The following 5 parameters were assessed: soft tissue swelling (an increase of 8 or more mm at the level of the tarsometatarsal joint); demineralization of the calcaneus; periarticular erosion of the tarsal bones; joint space narrowing of the interphalangeal joints; and periosteal reaction at the distal tibia. Each of these parameters was assessed as being present (score of 1) or absent (score of 0). A total score of 5 was possible for each hindleg assessed. Severity of each parameter was not assessed.

(b) Histopathologic analysis

Following the completion of the X-rays, the hindlegs were subjected to decalcification "en bloc" for three weeks to permit cutting of the bones with preservation of the tibiotalar joint. Blocks of the ankle joint were further decalcified in a 3% hydrochloric acid solution for 2 days. The blocks were embedded in paraffin and stained with hematoxylin-eosin. The articular changes were categorized as follows: soft tissue changes including those of the synovium and periarticular soft tissue; bone changes including both destructive and reactive alterations; and articular changes with particular emphasis on the articular cartilage, pannus formation, ankylosis and joint obliteration. Changes of each parameter were evaluated as being absent, mild, medium or severe and were scored as 0, 1, 2 and 3 respectively so that a maximum score of 9 was possible for each hindleg assessed.

Statistical analysis

Differences in hind paw edema volumes and body weight gains between treatment groups were evaluated by Student's "t" test. Differences in the radiographic changes were evaluated by Fisher's exact probability test. The significance of differences in the histopathologic and hindleg function scores was determined by the Mann-Whitney U-test.

EXAMPLE 1

The maximum tolerated doses of both etodolac and naproxen under the conditions of the experiment are 16 mg/kg and that of ibuprofen 100 mg/kg. In this study half the maximum tolerated dose was used, i.e., etodolac and naproxen at 8 mg/kg and ibuprofen at 50 mg/kg. These doses did not produce any signs of gastrointestinal irritation or any other ill effects and were considered comparable in relation to toxicity.

Treatment was started on day 16 after injection of the adjuvant. At that time all the groups of arthritic rats formed as described above showed comparable severity of symptoms.

Effect on hindpaw edema volume

All three drugs reduced the increase in hindpaw volume (edema) present at the start of the treatment period. This effect is shown in FIG. 2. In the non-treated rats, paw swelling continued to increase rapidly until about day 58 after adjuvant but then it declined to equilibrium values between days 72-100. The most important drug induced reduction of edema volume occurred during the first 28 days of treatment (day 16 to day 44 after adjuvant). During that period the antiedema effect of etodolac was significantly (P<0.01) superior to that of naproxen. After 56 days of treatment (day 72 after adjuvant) the paw volumes of the etodolac and naproxen treated groups remained about constant and were not statistically different for the remainder of the treatment period. Thus the antiedema effect of etodolac developed faster than that of naproxen, but eventually the effect of both drugs was comparable. However the reduction of edema produced by etodolac was significantly greater than that of ibuprofen throughout the treatment period.

Effect of hindleg function

Figure 3:
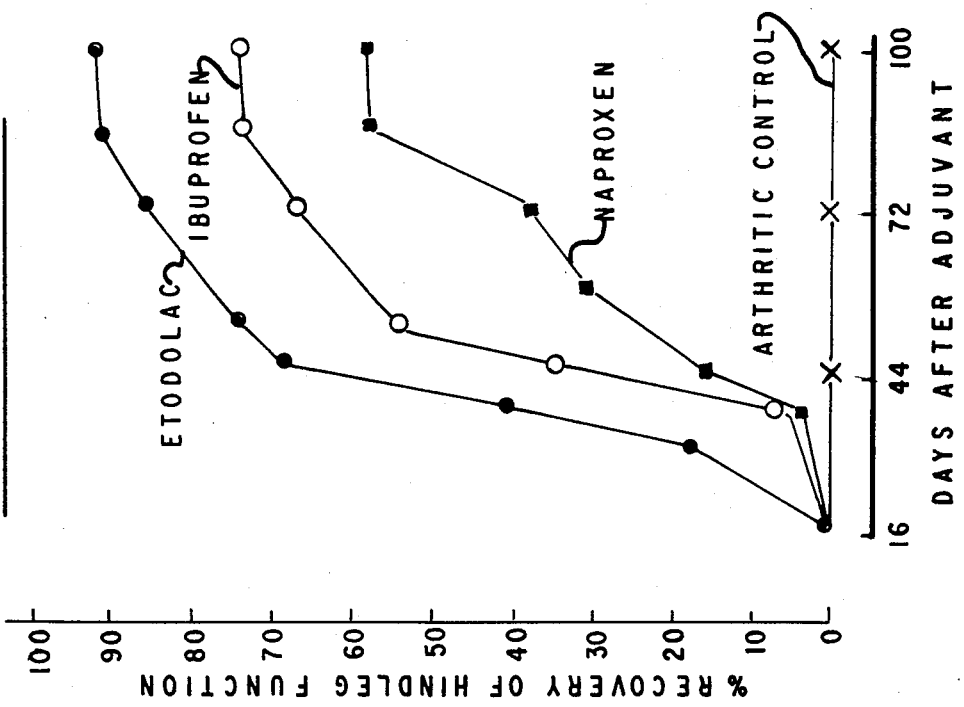

By day 16 after adjuvant all the arthritic rats had lost hindleg function. Without treatment there was no recovery. However, drug treatment produced a progressive recovery of hindleg function (FIG. 3). With etodolac, recovery was evident after 14 days of treatment while it took 21 to 28 days of dosage for it to appear with naproxen and ibuprofen. The effect of etodolac was statistically superior to that of naproxen until day 72 of the experiment (56 days of treatment). However the recovery produced by etodolac was statistically greater than that of ibuprofen at all time periods. On day 44 the recovery of hindleg function was 70% with etodolac, 36% with naproxen and 16% with ibuprofen. On the last day of the experiment it was 94%, 75% and 58% respectively.

Effect on body weight

Figure 4:
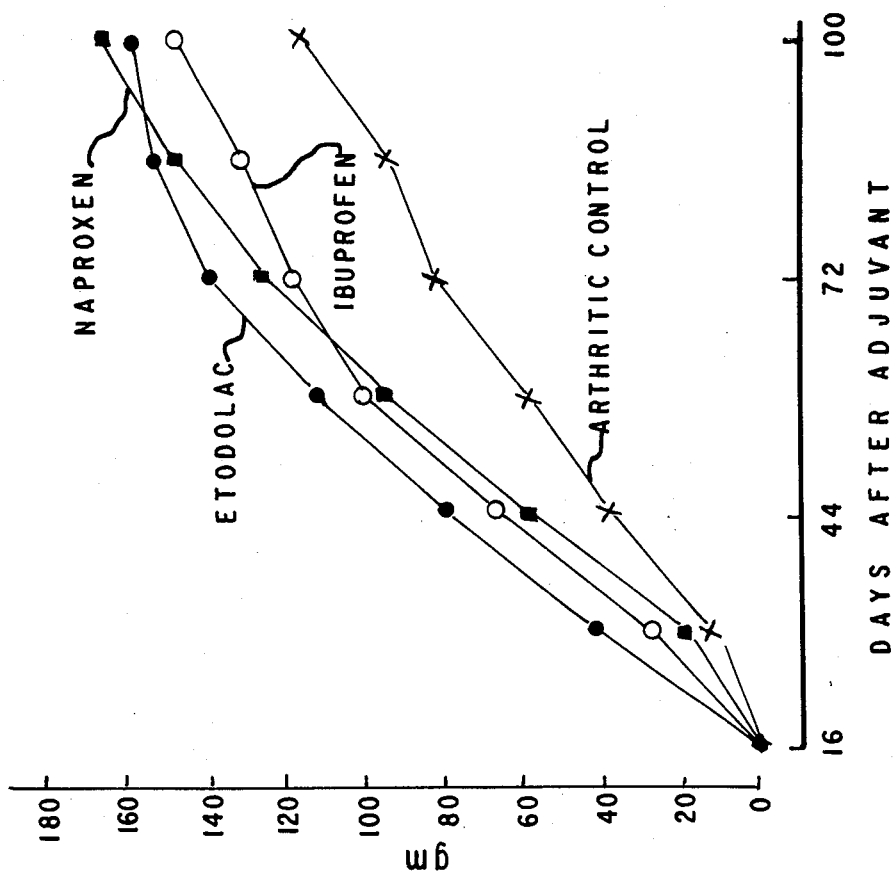

All drug treatments improved body weight gains compared with those of the untreated animals (FIG. 4). The body weight of the etodolac group increased more rapidly than that of the two other drugs until about day 72 after adjuvant. On day 86 there was no difference between the etodolac group and the ibuprofen group and by day 100 there was no difference between the three drug treated groups.

Radiologic analysis

Figure 5:
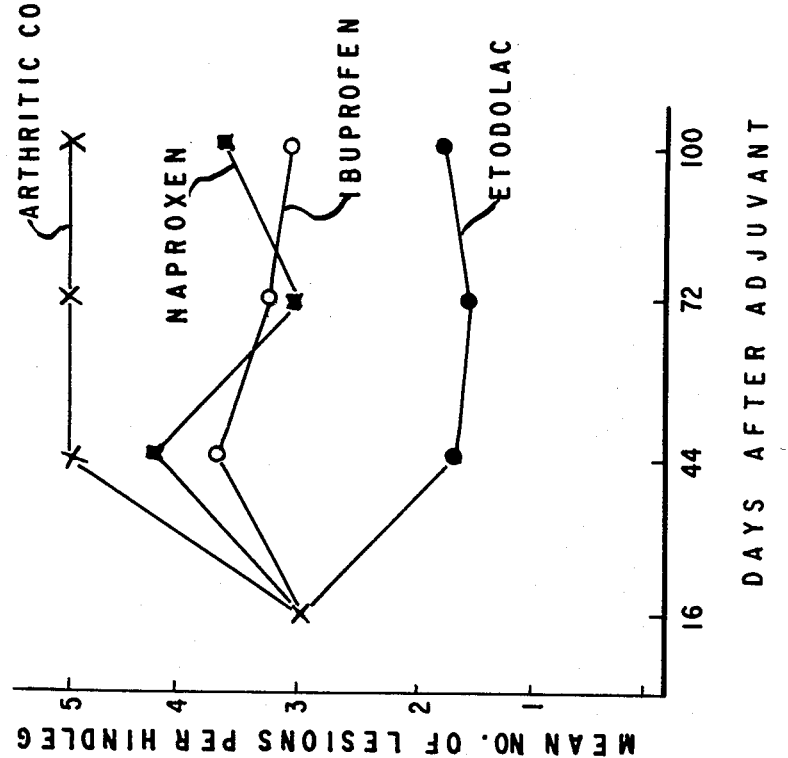

The details of the radiologic analysis are given in Table 1 and the mean number of lesions per hindpaw on the different assessment days is shown graphically in FIG. 5. On day 16 after adjuvant, before initiation of treatment, the hindlegs of the group of arthritic rats were assessed to have 61% of the total possible number of lesions (i.e mean hindleg lesion score=3.06; max score=5.00). Soft tissue swelling was present in all the hindlegs and periarticular erosion of the tarsal bones in most of the hindlegs. At that time period the incidence of the other lesions measured was relatively low. In the untreated rats, on the subsequent assessment days, every hindleg was positive for all of the 5 types of lesions evaluated and by day 44 after FCA the articular structures were totally destroyed.

In the rats dosed from day 16 with etodolac and evaluated on day 44, 72 and 100, the incidence of 4 out of the 5 types of lesions examined was lower than in the group examined on day 16. Only periarticular erosion of the tarsal bones was not consistently reduced. The mean number of lesions per hindleg was significantly lower in etodolac treated rats than in the rats assessed on day 16, before the initiation of treatment. Thus etodolac appeared to produce a reduction of most of the bone damage present in arthritic rats 16 days after the injection of the adjuvant.

Naproxen was not as effective as etodolac. The drug prevented the lesions from increasing to maximum and kept the incidence at about the level of day 16. Only on day 100 (84 days of treatment) was the incidence of soft tissue swelling and joint space narrowing significantly lowered below that of day 16. The mean number of lesions per hindleg on day 44 was slightly higher than on day 16 and about the same as on day 72 and day 100. Thus naproxen appeared to slow or arrest the progression of the bone lesions but not to reduce significantly the number of lesions present on day 16.

After 28 days of treatment with ibuprofen, the incidence of only one type of lesion (joint space narrowing) was significantly lower than in untreated rats and the mean number of lesions per hindpaw was only slightly lower. Thus ibuprofen merely prevented the arthritis from progressing to total destruction of the articular structures. It was more effective after 56 and 84 days of treatment. However, there was very little indication of a reduction of established lesions. As with etodolac, periarticular erosion of the tarsal bones was not affected by either naproxen or ibuprofen.

After 28 days of treatment 81% of the hindpaws of the etodolac treated rats were scored 2 or less, indicating a marked protection, while only 19% of the hindpaws of the naproxen group and 0% of the ibuprofen group were given a similar score. Furthermore 56% of the hindpaws of the ibuprofen group showed all the lesions (score of 5) indicating no protection while 31% of the naproxen and none of the etodolac treated hindpaws showed maximum incidence of lesions.

Treating with etodolac until day 100 did not produce any further improvement compared to day 44. With naproxen the extended treatment period appeared to produce a slight additional effect. The effects of ibuprofen were clearly better on day 72 and only slightly better on day 100 than on day 44. However the effects of etodolac were markedly superior to those of naproxen and ibuprofen on any assessment day.

Histopathologic analysis

Figure 6:
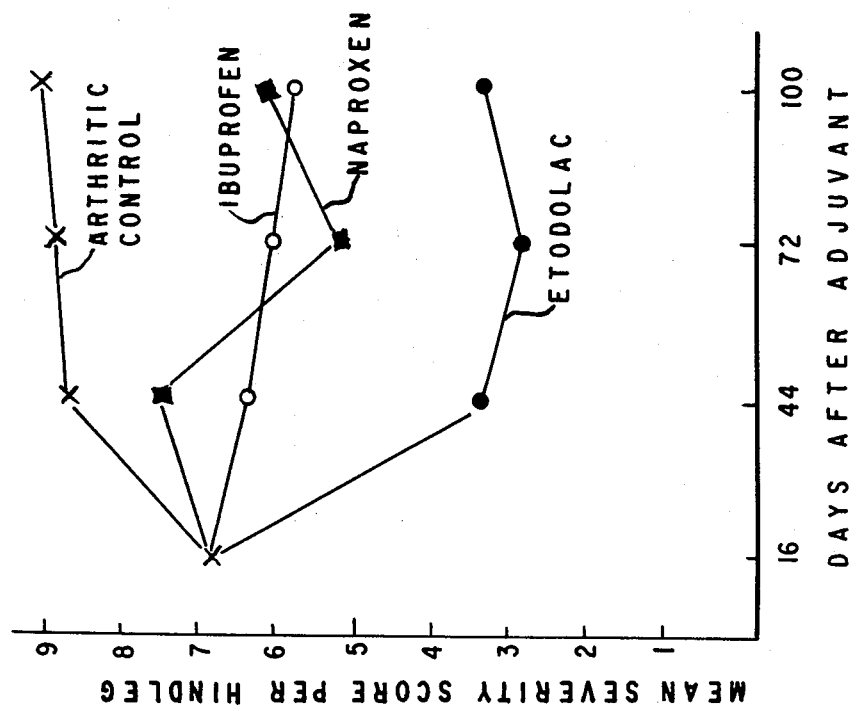

The details of the histopathologic assessment are given in Table 2 and mean severity scores per hindleg are summarized in FIG. 6. On day 16 of the disease, before the start of drug treatment, the severity of soft tissue changes was near maximum and that of bone and articular slightly below maximum. At subsequent assessment days, in untreated rats, the severity of the lesions was maximum or very near maximum.

After drug treatment, the histopathologic analysis gave results comparable to those obtained by radiologic assessment. Etodolac decreased significantly the severity of the soft tissue and articular changes below those present on day 16 and kept bone changes slightly below that of day 16. Naproxen reversed the soft tissue changes, prevented bone changes from reaching maximum values and kept articular changes at about the same severity as on day 16. Ibuprofen was less active than naproxen after 28 days of treatment, more active after 56 days and showed a comparable activity after 84 days.

The mean severity score per hindleg, of the etodolac treated rats at any assessment day was significantly lower than that of the rats evaluated on day 16. Naproxen reduced the mean severity score slightly below that of day 16. However, the reduction did not reach statistical significance. Ibuprofen reduced significantly the mean histopathologic score below that of day 16 only on the assessment made on day 72.

Extending the treatment period with etodolac did not produce an obvious improvement. The effects of naproxen and ibuprofen were slightly improved. The effects of etodolac were superior to those of naproxen and ibuprofen at any time period.

Normal rats did not show any radiographic or histopathologic lesions.

Effect of stopping drug treatment

When treatment with the 3 drugs was stopped on day 44 after 28 days of dosing and the evaluation of the groups made on day 72, after a further 28 day period without treatment, some of the signs of the disease and the pathological scores were greater in these groups than in those which received treatment during the entire period (Table 3). There was no significant recurrence of the edematous reaction in the etodolac group but there was a slight recurrence in the naproxen group and a pronounced effect in the ibuprofen rats.

When the rats were examined individually, obvious signs of recurrence of the disease process were found in 3 etodolac, 3 naproxen and 4 ibuprofen treated rats (Table 4). These rats showed lower body weight gains between day 44 and 72, lower hindleg function scores and higher pathology scores on day 72. None of the rats treated with etodolac showed a significant increase in edema between day 44 and 72. However the 4 ibuprofen and 1 naproxen treated rats showed a marked increase (0.5 to <1 ml) in hindpaw volume during the same time period. All the rats whowing a recurrence of edema had maximum radiologic and histopathologic scores.

Thus some rats did not show any signs of relapse when treatment was stopped on day 44. Others showed a limited increase in pathological scores but no increase in paw volume when compared to treated rats. Finally in some rats there was a marked recurrence of edema which was associated with high bone and articular damage. When relapse occurred it was less extensive in the etodolac and naproxen treated rats than in the rats receiving ibuprofen.

Although average scores were slightly higher in the untreated rats when drug treatment was stopped on day 72 after 56 days, there were no obvious signs of recurrence in any of the rats of the three treatment groups (Table 3).

TABLE 1

Results of the radiologic assessment made at the end of the different treatment schedules. Treatment was started on day 16 after the injection of the adjuvant.

| Drug (mg/kg) | (n) | Day of Assessment (days of treatment) | % of hindlegs assessed to be positive for: | | | | | Mean number of lesions per hindleg (max = 5) |
| --- | --- | --- | --- | --- | --- | --- | --- | --- |
| | | | Soft Tissue Swelling | Periarticular erosion (tarsus) | Bone demineralization (calcancus) | Periosteal reaction (distal tibia) | Joint Space narrowing (interphalangeal) | |
| Control | 8 | 16(—) | 100 | 81 | 31 | 38 | 57 | 3.06 |
| | 8 | 44(—) | 100 | 100 | 100 | 100 | 100 | 5.00 |
| | 8 | 72(—) | 100 | 100 | 100 | 100 | 100 | 5.00 |
| | 8 | 100(—) | 100 | 100 | 100 | 100 | 100 | 5.00 |
| Etodolac (8) | 8 | 44(28) | 69+ | 69* | 19*** | 0++ | 13++ | 1.69+++ |
| | 8 | 72(56) | 38+++ | 94 | 6*** | 13*** | 6++ | 1.56+++ |
| | 8 | 100(84) | 56++ | 94 | 13*** | 13*** | 6++ | 1.81+++ |
| Naproxen (8) | 8 | 44(28) | 100 | 100 | 69* | 56** | 50*** | 3.75*** |
| | 8 | 72(56) | 88 | 100 | 100 | 63** | 25*** | 44*** | 3.19*** |
| | 8 | 100(84) | 63++ | 100 | 63** | 75* | 13++ | 3.12*** |
| Ibuprofen (50) | 8 | 44(28) | 100 | 100 | 81 | 81 | 69* | 4.31** |
| | 8 | 72(56) | 88 | 94 | 75** | 31*** | 19+ | 3.06*** |

TABLE 1-continued

Results of the radiologic assessment made at the end of the different treatment schedules. Treatment was started on day 16 after the injection of the adjuvant.

| Drug (mg/kg) | (n) | Day of Assessment (days of treatment) | % of hindlegs assessed to be positive for: | | | | | Mean number of lesions per hindleg (max = 5) |
|---|---|---|---|---|---|---|---|---|
| | | | Soft Tissue Swelling | Periarticular erosion (tarsus) | Bone demineralization (calcancus) | Periosteal reaction (distal tibia) | Joint Space narrowing (interphalangeal) | |
| | 6 | 100(84) | 92 | 100 | 67** | 75 | 33*** | 3.67*** |

+ Incidence of the lesions significantly lower than arthritic controls on day 16 + $P < 0.05$,
++$P < 0.01$ and
+++$P < 0.001$
*Incidence of the lesions significantly lower than arthritic controls on the corresponding day
*$P < 0.05$,
**$P < 0.01$ and
***$P < 0.001$.
Note:
the mean number of lesions per hindleg of the etodolac treated rats is significantly lower than that of the two other drugs at any assessment day $P < 0.01$

TABLE 2

Results of the histopatholigic assessment made at the end of the different treatment schedules. Treatment was started on day 16 after the injection of the adjuvant.

| Drug (mg/kg) | n | Day of assessment (days of (treatment) | % of Maximum Histopathologic severity score | | | Mean severity score per hindleg (max = 9.00) |
|---|---|---|---|---|---|---|
| | | | Soft Tissue | Bone | Articular | |
| Control | 8 | 16(—) | 96 | 67 | 69 | 6.94 |
| | 8 | 44(—) | 96 | 100 | 96 | 8.75 |
| | 8 | 72(—) | 96 | 100 | 100 | 8.88 |
| | 8 | 100(—) | 100 | 100 | 100 | 9.00 |
| Etodolac (8) | 8 | 44(28) | 27+++ | 52*** | 33+++ | 3.37+++ |
| | 8 | 72(56) | 19+++ | 54*** | 25+++ | 2.94+++ |
| | 8 | 100(84) | 27+++ | 56*** | 29+++ | 3.37++ |
| Naproxen (8) | 8 | 44(28) | 60+++ | 88 | 67*** | 6.44*** |
| | 8 | 72(56) | 64+++ | 77*** | 58*** | 6.00*** |
| | 8 | 100(84) | 58+++ | 81*** | 56*** | 5.87*** |
| Ibuprofen | 8 | 44(28) | 83+ | 94 | 73*** | 7.50*** |
| | 8 | 72(56) | 58+++ | 60*** | 56*** | 5.25++ |
| | 6 | 100(84) | 58+++ | 78*** | 69*** | 6.17*** |

+ Severity of the lesions significantly lower than arthritic controls on day 16:
+ $P < 0.05$
++ $P < 0.01$ and
+++ $P < 0.001$.
Severity of the lesions significantly lower than arthritic controls on the corresponding day;
*$P < 0.05$,
**$P < 0.01$ and
***$P < 0.001$.
Note:
The mean number of lesions per hindleg of the etodolac-treated rats is significantly lower than that of the two other drugs at any assessment day $P < 0.01$.

TABLE 3

Comparison of the measurements of the different parameters of adjuvant arthritis studied in the group of rats which were treated until the day of assessment and that which was 28 days without treatment before assessment.

| Drug (mg/kg) | n | Treatment period day after adj. | Day of assessment | Edema volume ml ± S.E. | Body weight gain from day 16 gm ± S.E. | Hindleg function % recovery | Radiologic score mean per hindleg | Histopathologic score mean per hindleg |
|---|---|---|---|---|---|---|---|---|
| Etodolac (8) | 8 | 16–72 | 72 | 0.38 ± 0.06 | 142 ± 3 | 88 | 1.56 | 2.94 |
| | 8 | 16–44 | 72 | 0.44 ± 0.06 | 120 ± 9* | 63 | 2.25* | 4.91** |
| | 8 | 16–100 | 100 | 0.43 ± 0.04 | 161 ± 8 | 94 | 1.81 | 3.37 |
| | 8 | 16–72 | 100 | 0.47 ± 0.06 | 178 ± 7 | 87 | 2.00 | 3.62 |
| Naproxen (8) | 8 | 16–72 | 72 | 0.42 ± 0.05 | 120 ± 3 | 81 | 3.19 | 6.00 |
| | 8 | 16–44 | 72 | 0.69 ± 0.11* | 114 ± 5 | 31* | 3.62 | 6.94** |
| | 8 | 16–100 | 100 | 0.54 ± 0.07 | 151 ± 4 | 75 | 3.12 | 5.87 |
| | 8 | 16–72 | 100 | 0.61 ± 0.05 | 161 ± 7 | 69 | 3.31 | 6.12 |
| Ibuprofen (50) | 8 | 16–72 | 72 | 0.80 ± 0.07 | 123 ± 4 | 44 | 3.06 | 5.31 |
| | 7 | 16–44 | 72 | 1.48 ± 0.31** | 88 ± 7** | 21 | 4.07* | 7.57** |
| | 6 | 16–100 | 100 | 0.72 ± 0.12 | 167 ± 5 | 58 | 3.67 | 6.17 |
| | 7 | 16–72 | 100 | 0.72 ± 0.08 | 156 ± 5 | 29 | 3.85 | 6.64 |

*indicates a significant ($P < 0.05$) and
**($P < 0.01$) difference between the groups treated from day 16 to day 44 and that treated from day 16 to day 72.

TABLE 4

Incidence and severity of recurrence of adjuvant arthritis in rats after a period of 28 days without treatment. The rats had received drug treatment from day 16 to 44 after injection of the adjuvant.

| Drug and (No. of rats) | No. of rats without any signs of relapse | No. of rats with limited signs of relapse[1] | No. of rats in which the disease was back to maximum intensity[2] |
|---|---|---|---|
| Etodolac (8) | 5 | 3 | 0 |
| Naproxen (8) | 5 | 2 | 1 |
| Ibuprofen (7) | 3 | 0 | 4 |

[1] No recurrence of edema but higher pathological scores.
[2] Marked recurrence of edema (>0.5 ml) and maximum radiologic and histopathologic scores.

EXAMPLE 2

Severity of adjuvant arthritis before drug treatment (day 16).

On day 16 after injection of FCA, prior to drug treatment, all the groups of six arthritic rats that were formed during these experiments showed comparable severity of symptoms. The mean hind paw edema volumes did not differ by more than 0.3 ml and the mean body weights did not differ by more than 16 g. In the normal control groups, there was no measurable increase in hind paw volume between day 0 and day 16. However, due to the growth-retarding effect of the adjuvant-induced disease, the body weights of the normal controls were significantly higher than those of the arthritic rats. All the arthritic animals showed total loss of normal hind limb function.

Comparison of the effect of drug treatment on the symptoms of adjuvant arthritis.

The values for the hind paw edema volume, body weight gain and the number of rats with normal hind leg function on day 30 for the groups which were to be evaluated for bone and articular damage on that day (30-day exp.) and those that were treated until day 44 (44-day exp.) are shown in Table 5. The mean paw edema volumes of the arthritic control rats were the same in the two experiments and the volume increased by 1 ml between day 16 and day 30 indicating a relatively rapid development of the disease during that time period. The effect of drug treatment on the edema was very similar in the two experiments. The only statistically significant difference in edema volumes (0.2 ml) between the 30 day experiment and the 44 day experiment occurred between the two groups treated with aspirin 300 mg/kg. Body weight gains were slightly higher in the 44-day experiment. In both experiments, recovery of normal hind limb function occurred only in the groups treated with the high dose of etodolac. Thus, on day 30, both the severity of the arthritis and the responses to drug treatment (as judged by hind paw edema, and the number of animals showing normal hind leg function) were comparable in both experiments. Therefore, a comparison of the pathological lesions assessed on day 30 (after 14 days of treatment) with those measured on day 44 (after 28 days of treatment) was considered valid.

Among the treated groups, only the animals which received aspirin 150 mg/kg exhibited edema volumes on days 30 and 44 that were not reduced below the pretreatment reading. Furthermore, this dose of aspirin did not significantly increase the body weight gains after 14 or 28 days of treatment. In all of the other groups, drug treatment markedly reduced the edema volumes below day 16 readings and on day 44, the paw volumes of animals treated with etodolac 8 mg/kg were down to values approaching normal. Body weight gains were increased significantly over those of the untreated arthritic animals. All treatments except aspirin 150 mg/kg induced a recovery of normal hind limb function in some of the rats but etodolac 8 mg/kg was the only treatment which induced a recovery in half the rats by day 30 and recovery in all rats by day 44.

Assessment of bone and articular lesions (a) Radiographic analysis. The incidence of bone demineralization, periosteal reaction, joint space narrowing, periarticular erosion, and soft tissue swelling at the level of the ankle joint of the rats of each treatment group was determined and the number of rats assessed to be positive for each of these lesions is presented in Table 6. In the arthritic control group on day 16, one animal exhibited bone demineralization and one rat was positive for periosteal reaction. However, most of these animals exhibited joint space narrowing and all showed periarticular erosion of the tarsal bones and soft tissue swelling. By day 30, all arthritic control animals exhibited all five lesions. Between day 30 and 44, the incidence of the lesions assessed remained at maximum but the lesions became more severe and extensive, spreading to the metatarsal and phalangeal bones. However, the severity of the lesions and the damage to the metatarsal and phalangeal bones were not considered in this study. Normal animals showed none of these lesions.

Treatment with etodolac between day 16 and 30, protected a number of rats against the development of bone demineralization and periosteal reaction and caused other established lesions to regress (soft tissue swelling and joint space narrowing). However, erosion of the tarsal bones was prevented in one rat only.

TABLE 5

Mean hind paw volumes and body weight gains and the number of rats with normal hind leg function on the different assessment days

| Treatment and daily oral dose[a] (mg/kg) | Day after FCA | Mean edema volume ml ± SE | | Mean body weight gain from day 16 g ± SE | | No. of rats with normal hind leg function | |
|---|---|---|---|---|---|---|---|
| | | 30 day experiment | 44 day experiment | 30 day experiment | 44 day experiment | 30 day experiment | 44 day experiment |
| Normal control | 16 | 0 | 0 | | | 6 | 6 |
| | 30 | 0 | 0 | 25 ± 1 | 25 ± 3 | 6 | 6 |
| | 44 | | 0 | | 47 ± 6 | | 6 |
| Arthritic control | 16 | 1.4 ± 0.1 | 1.4 ± 0.2 | | | 0 | 0 |
| | 30 | 2.4 ± 0.2 | 2.4 ± 0.2 | −7 ± 3 | 12 ± 2* | 0 | 0 |
| | 44 | | 2.9 ± 0.2 | | 25 ± 4 | | 0 |
| Etodolac (8) | 16 | 1.6 ± 0.1 | 1.3 ± 0.1 | | | 0 | 0 |
| | 30 | 0.5 ± 0.1 | 0.4 ± 0.1 | 38 ± 7 | 40 ± 4 | 4 | 3 |
| | 44 | | 0.2 ± 0.06 | | 77 ± 6 | | 6 |

TABLE 5-continued

Mean hind paw volumes and body weight gains and the number of rats with normal hind leg function on the different assessment days

| Treatment and daily oral dose[a] (mg/kg) | Day after FCA | Mean edema volume ml ± SE | | Mean body weight gain from day 16 g ± SE | | No. of rats with normal hind leg function | |
|---|---|---|---|---|---|---|---|
| | | 30 day experiment | 44 day experiment | 30 day experiment | 44 day experiment | 30 day experiment | 44 day experiment |
| Etodolac (4) | 16 | 1.3 ± 0.1 | 1.5 ± 0.3 | | | 0 | 0 |
| | 30 | 0.8 ± 0.1 | 0.7 ± 0.08 | 20 ± 5 | 34 ± 4* | 0 | 0 |
| | 44 | | 0.4 ± 0.08 | | 66 ± 5 | | 4 |
| Aspirin (300) | 16 | 1.4 + 0.1 | 1.3 ± 0.1 | | | 0 | 0 |
| | 30 | 1.0 ± 0.04 | 0.8 ± 0.06* | 11 ± 2 | 22 ± 3* | 0 | 0 |
| | 44 | | 0.7 ± 0.06 | | 52 ± 3 | | 3 |
| Aspirin (150) | 16 | 1.4 ± 0.1 | 1.3 ± 0.1 | | | 0 | 0 |
| | 30 | 1.7 ± 0.1 | 1.7 ± 0.1 | 2 ± 4 | 10 ± 2 | 0 | 0 |
| | 44 | | 1.8 ± 0.06 | | 31 ± 4 | | 0 |
| Naproxen (8) | 16 | | 1.4 ± 0.2 | | | | 0 |
| | 30 | | 0.7 ± 0.1 | | 24 ± 3 | | 0 |
| | 44 | | 0.4 ± 0.1 | | 61 ± 6 | | 3 |

[a]Drug treatment was started on day 16. There were six rats in each group.
*Different from the 30 day exp. ($p < 0.05$).
Note: Except for weight gain with aspirin 150 mg/kg, all the edema volumes and weight gains are significantly different ($p < 0.05$) from those of the arthritic control group.

TABLE 6

Number of arthritic rats which were found to have lesions upon radiographic analysis of the right hind leg. Five types of lesions were assessed on different days after induction of arthritis. There were six rats in each treatment group.

| Treatment and daily oral dose[a] (mg/kg) | Day after FCA | Number of rats assessed to be positive | | | | | No. of radiographic lesions Total | Mean |
|---|---|---|---|---|---|---|---|---|
| | | Bone demineralization | Periosteal reaction | Joint space narrowing | Periarticular erosion | Soft tissue swelling | | |
| Arthritic control | 16 | 1 | 1 | 5 | 6 | 6 | 19 | 3.16 |
| | 30 | 6 | 6 | 6 | 6 | 6 | 30 | 5.00 |
| | 44 | 6 | 6 | 6 | 6 | 6 | 30 | 5.00 |
| Etodolac (8) | 30 | 3 | 3 | 4 | 5 | 2 | 17* | 2.83 |
| | 44 | 2 | 0 | 2 | 5 | 1 | 10*+ | 1.66 |
| Etodolac (4) | 30 | 5 | 4 | 3 | 6 | 3 | 21* | 3.50 |
| | 44 | 2 | 2 | 5 | 5 | 1 | 15* | 2.50 |
| Aspirin (300) | 30 | 4 | 5 | 6 | 6 | 6 | 27 | 4.50 |
| | 44 | 5 | 4 | 6 | 6 | 4 | 25 | 4.16 |
| Aspirin (150) | 30 | 6 | 6 | 6 | 6 | 6 | 30 | 5.00 |
| | 44 | 6 | 6 | 6 | 6 | 6 | 30 | 5.00 |
| Naproxen (8) | 44 | 4 | 2 | 5 | 4 | 3 | 18* | 2.85 |

[a]Drug treatment was started on the 16th day after FCA.
*Different from arthritic control $p < 0.01$
+Different from day 16 arthritic control $p = 0.014$ On day 44, after 28 days of treatment with etodolac, the number of rats positive for bone demineralization, periosteal reaction and joint space narrowing (high dose) was less than that obtained after 14 days of treatment (day 30). Further, the incidence of soft tissue swelling, joint space narrowing (high dose), periosteal reaction (high dose) and periarticular erosion was less than on day 16 indicating not only a slowing down of the pathological changes associated with the arthritis but an actual reversal of the arthritic condition.

Aspirin (300 mg/kg) administered for 14 or 28 days protected a few rats against demineralization and periosteal reaction but had no effect on the incidence of joint space narrowing and periarticular erosion. Soft tissue swelling was reduced only after 28 days of treatment. At 150 mg/kg, aspirin did not affect the incidence of any of the lesions assessed. Naproxen was studied only after 28 days of treatment. It reduced the incidence of demineralization, periosteal reaction and periarticular erosion. It caused reversal of soft tissue swelling in half the rats, but the effect on joint space narrowing was minimal.

Etodolac and naproxen produced a statistically significant reduction of the total number of radiographic lesions and the response with etodolac was dose related. In fact on day 44 the group treated with 8 mg/kg of etodolac showed significantly fewer lesions ($p=0.014$) than the group assessed on day 16 prior to the start of drug treatment. Furthermore 8 mg/kg of etodolac was significantly more effective ($p=0.025$) than naproxen at the same dose. At the dose used the latter drug halted the progression of the disease, but did not reverse it. Aspirin (300 mg/kg) produced some protective effect; however, the reduction was not statistically significant.

(b) Histopathologic analysis. The results of the histopathologic study of the soft tissue, bone and articular changes are presented in Table 7. In the untreated rats, the soft tissue changes were scored maximal on days 16 and 44 although not on day 30. Bone changes were mild on day 16, but became maximal by day 30. Articular changes increased progressively between day 16 and day 44.

The 8 mg/kg dose of etodolac produced a marked reduction in the severity of all the lesions evaluated. The further development of bone damage and articular changes was minimized and the severity of soft tissue damage was reduced. Etodolac 4 mg/kg and naproxen were effective against the lesions studied, but appreciably less effective than etodolac 8 mg/kg. The 300 mg/kg dose of aspirin produced a slight but not significant effect on these variables. The group which received aspirin 150 mg/kg did not differ from the untreated control group. Naproxen and both doses of etodolac produced a significant reduction of the total histopathologic score.

The radiographic and histologic techniques afforded comparable results, but the latter method of evaluation appeared more stringent. Thus, the results of the radiographic method suggested that aspirin 300 mg/kg at least reduced the severity of the lesions if not the incidence, but histopathologic evaluation indicated that the drug was totally inactive at this dose. Etodolac 4 mg/kg and naproxen also appeared less active by the histologic method than by the radiologic analysis. However, both methods demonstrated that etodolac 8 mg/kg was highly effective in preventing the articular and bone damage characteristic of adjuvant-induced arthritis.

TABLE 7

Results of the histopathologic evaluation of the right hind leg of arthritic rats which were previously assessed radiographically.

| Treatment and daily oral dose[a] (mg/kg) | Day after FCA | Histopathologic score | | | | |
|---|---|---|---|---|---|---|
| | | Soft tissue | Bone | Articular | Total | Mean |
| Arthritic control | 16 | 18 | 6 | 8 | 32 | 5.33 |
| | 30 | 13 | 18 | 15 | 46 | 7.66 |
| | 44 | 18 | 18 | 18 | 54 | 9.00 |
| Etodolac 8 | 30 | 6 | 9 | 8 | 23* | 3.83 |
| | 44 | 6 | 8 | 9 | 23* | 3.84 |
| Etodolac 4 | 30 | 12 | 14 | 8 | 34* | 5.66 |
| | 44 | 44 | 14 | 12 | 40* | 6.66 |
| Aspirin 300 | 30 | 12 | 16 | 15 | 43 | 7.16 |
| | 44 | 18 | 18 | 18 | 54 | 9.00 |
| Asprin 150 | 30 | 12 | 16 | 18 | 46 | 7.66 |
| | 44 | 18 | 18 | 18 | 54 | 9.00 |
| Naproxen 8 | 44 | 12 | 16 | 15 | 43* | 7.16 |

[a]Drug treatment was started on the 16th day after FCA. There were six rats in each group.
*Different from arthritic control p < 0.01.

A number of antiinflammatory drugs have been shown to limit the bone and articular pathology associated with adjuvant arthritis in rats. Etodolac, a novel antiinflammatory drug established to be safe and effective in patients with rheumatoid arthritis and osteoarthritis has been shown to alter the course of the adjuvant disease in the present invention. When treatment with etodolac (8 mg/kg) was started 16 days after the initiation of the disease, the number of radiologic lesions present after 28 days of treatment was significantly lower than in the arthritic rats evaluated before the start of treatment. Furthermore, the incidence of the lesions decreased by almost 40% between the 14th and the 28th day of treatment. In the same experiment, naproxen prevented the lesions from increasing but did not reduce the incidence below that of day 16.

In the present invention this apparent reversal of the bone and articular pathology produced by etodolac was studied extensively. The treatment period extended to 84 days (from day 16 to day 100 after FCA). In addition, in order to make sure that the effects of long term treatment were drug related and to establish whether reduction of bone damage was permanent, treatment was stopped in some groups after either 28 or 56 days and the evaluation of bone pathology made 28 days later. Two clinically used antiinflammatory drugs, naproxen and ibuprofen, were studied under the same protocol. All three drugs were given daily at half the maximum tolerated dose, i.e. etodolac and naproxen at 8 mg/kg and ibuprofen at 50 mg/kg. Other parameters of adjuvant arthritis (hindpaw edema, hindleg function and weight gains) were also studied.

The reduction of the established lesions produced by etodolac was very evident. The incidence of 4 out of the 5 radiologic lesions assessed was decreased below that of day 16. In the histopathologic study soft tissue and articular changes were significantly lower than on day 16. The mean number of radiologic lesions per hindleg and the mean severity scores in the histopathologic analysis were significantly lower than in the group of rats evaluated on day 16.

Naproxen and ibuprofen were not as effective as etodolac. Naproxen reversed soft tissue changes in the histopathologic analysis but the other lesions were either prevented from reaching maximum scores or from increasing above the level on day 16. Total scores were not reduced below day 16 values. Ibuprofen produced an even weaker protective effect than naproxen. Extending the treatment period to day 72 or day 100 after FCA (56 or 84 days of drug dosing) did not improve further the effect of etodolac. However, the low incidence of bone and articular damage was held constant. The effects of naproxen were slightly increased when the treatment period lasted 56 days. Ibuprofen produced a much better protective action after 56 days of treatment than after 28 and 84 days of dosing. This unexpected low score after 56 days of treatment was in part due to two rats which had abnormally mild pathology.

Stopping treatment on day 44 and assessing the lesions 28 days later (day 72 after FCA) resulted in a resurgence of the disease in some of the rats of the three treatment groups. In the ibuprofen treated groups the recurrence was associated with a return of the edematous reaction and severe pathological changes in all affected rats. The etodolac and the naproxen treated rats showed milder signs of relapse which were not associated with a return of edema or severe bone and articular damage (except for one naproxen rat). However, if treatment was stopped after 56 days (day 72 after FCA) there were no clear signs of relapse in any of the rats of the three treatment groups. Thus 72 days after injection of the adjuvant the immunologic reaction responsible for the inflammatory response appeared to have subsided completely in all rats. In fact it appeared to have subsided completely in some of the rats and partly in others by day 44 after the induction of the disease.

It is unlikely that the antiinflammatory drugs used had any significant effect on the immune response to Freund's adjuvant. It is well known that these drugs lack classical immunosuppressive activity even though some type of action on immunoregulation cannot be ruled out. It is, however, interesting to note that etodolac, which was markedly more effective than ibuprofen on the parameters measured, appeared to induce a more rapid decrease of the immunologic reaction than ibuprofen. This effect may be secondary to its rapid onset of action and its more potent antiinflammatory activity.

Under the present experimental conditions mild to moderate pathological changes were present on day 16 after adjuvant, these changes were severe on day 30 and the articular and bone structures of the hindpaw were completely destroyed by day 44. When treatment with suitable doses of antiinflammatory drugs was started on day 16 the lesions were either partially reversed (etodolac) or prevented from progressing to maximum (naproxen and ibuprofen). When treatment was continued for a period of time longer than that of the immunological phenomenon responsible for the disease, the rats could be considered to have undergone a complete remission or to have been cured. The remaining lesions can be considered as residual pathology or sequealae. On day 100 the etodolac treated rats appeared normal (paw size, behavior, mobility, body weights, etc.); there were no visible signs of their former arthritic condition. When administered early enough in the course of the disease, antiinflammatory drugs can protect against complete articular destruction, but the effectiveness of the different drugs will determine the severity of the residual lesions. An effective rapid onset of action is probably very important in order to limit the extent of permanent damage. The effects of etodolac on edema, hindleg function and body weight developed more rapidly than those of naproxen and ibuprofen. A faster onset of action might be an important factor in the greater efficacy of etodolac in preventing permanent bone and articular damage. The results of the radiologic and histopathologic study also indicated a faster onset of action of etodolac. Maximum effects were obtained within 28 days of treatment. Further treatment did not produce a greater effect on joint damage but had a beneficial effect by preventing relapse and permitting further improvement in the general condition (weight gain, hindleg function) of the animals. The first 28 days of treatment appeared to be the most important of these experiments. It is during that time that the disease is the most active.

In the course of these experiments there was a particularly good correlation between the extent of articular damage and the recovery of hindleg function. Etodolac produced the most rapid and complete protection of articular pathology as well as the most rapid and complete recovery of hindleg function.

Adjuvant arthritis in rats does not duplicate exactly rheumatoid arthritis in man. The rat disease is characterized by a steady progression of articular damage ending in complete destruction within a period of 30 days after the first symptoms appear (a period probably comparable to about 2 years in man). The human condition may be progressive or remitting and last for a period of months to years. Bone and articular damage may be minimal or extensive. However, the pathological changes occurring at the tibiotarsal joint in the rat during the evolution of the disease are strikingly similar to those occurring in rheumatoid arthritis. K. D. Rainsford: Agents and Actions 12 452–458 (1982).

Thus, early treatment of rheumatoid arthritis with an antiinflammatory drug, shown to be very effective in the animal model, can have a similar beneficial effect on the articular pathology of rheumatoid arthritis.

In humans a daily dose of 25 to 1200 mg is well tolerated. A daily dose of 200 mg to 500 mg, taken in one or two equal doses, is used for the treatment of arthritis. L. Joubert, et al., Curr. Therap. Res. 32, 74–88 (1982).

To obtain remission of the disease in humans, according to the present invention, a daily dose in the upper tolerated range is required i.e., 600 mg to 1200 mg per day. The preferred daily dosage required to obtain remission of arthritis in humans is 500 mg twice daily or a total of 1000 mg per day.

In conclusion, etodolac produced a reduction of the mean lesion scores per hindleg below that present at the start of the treatment period. While equivalent doses in relation to tolerance of naproxen and ibuprofen prevented the lesions from increasing to maximum incidence and severity, they did not produce a consistant reduction of these lesions below that of day 16. The effects of etodolac on edema, hindleg function and body weight gains were also superior to those of the other two drugs. The onset of action of etodolac was faster than that of the other two drugs.

I claim:

1. A method for producing reversal of the articular pathology associated with arthritis in mammals, which comprises: administering to the arthritic mammal an effective amount of etodolac.

2. The method of claim 1 wherein the etodolac is administered at a daily dose ranging from 600 mg to 1200 mg.

3. The method of claim 2 wherein etodolac is administered at a dose of 500 mg twice daily or a total daily dose of 1000 mg.

* * * * *